US012709695B2

(12) United States Patent
Yamaguchi et al.

(10) Patent No.: US 12,709,695 B2
(45) Date of Patent: Aug. 18, 2026

(54) COATING FILM

(71) Applicant: DAIKIN INDUSTRIES, LTD., Osaka (JP)

(72) Inventors: Hiroki Yamaguchi, Osaka (JP); Kensuke Mohara, Osaka (JP); Gregory Tortissier, Osaka (JP); Masamichi Morita, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 776 days.

(21) Appl. No.: 16/756,528

(22) PCT Filed: Oct. 12, 2018

(86) PCT No.: PCT/JP2018/038129
§ 371 (c)(1),
(2) Date: Apr. 16, 2020

(87) PCT Pub. No.: WO2019/078115
PCT Pub. Date: Apr. 25, 2019

(65) Prior Publication Data
US 2020/0291257 A1 Sep. 17, 2020

(30) Foreign Application Priority Data
Oct. 18, 2017 (JP) ................................ 2017-202238

(51) Int. Cl.

| | |
|---|---|
| ***C09D 133/10*** | (2006.01) |
| ***C07C 49/10*** | (2006.01) |
| ***C07C 69/003*** | (2006.01) |
| ***C07C 255/67*** | (2006.01) |
| ***C09D 133/08*** | (2006.01) |

(52) U.S. Cl.
CPC ............ *C09D 133/10* (2013.01); *C07C 49/10* (2013.01); *C07C 69/003* (2013.01); *C07C 255/67* (2013.01); *C09D 133/08* (2013.01)

(58) Field of Classification Search
CPC .... C09D 133/10; C09D 133/08; C07C 49/10; C07C 69/003; C07C 255/67
See application file for complete search history.

(56) References Cited

U.S. PATENT DOCUMENTS

| | | | | |
|---|---|---|---|---|
| 2001/0027231 A1 | 10/2001 | Sugamoto et al. | | |
| 2004/0096663 A1* | 5/2004 | Yamaguchi | C08G 18/673 | 428/41.8 |
| 2006/0147674 A1* | 7/2006 | Walker, Jr. | C08J 7/0427 | 524/413 |

FOREIGN PATENT DOCUMENTS

| | | |
|---|---|---|
| CN | 1317038 | 10/2001 |
| CN | 101124273 | 2/2008 |
| CN | 102911530 | 2/2013 |
| CN | 104017487 | 9/2014 |
| CN | 106758215 | 5/2017 |
| EP | 2 813 521 | 12/2014 |
| JP | 4-254406 | 9/1992 |
| JP | 11-241047 | 9/1999 |
| JP | 2001-131318 | 5/2001 |
| JP | 2008-56789 | 3/2008 |
| JP | 2010-89373 | 4/2010 |
| JP | 2010-235783 | 10/2010 |
| JP | 2012-246389 | 12/2012 |
| WO | 2006/073856 | 7/2006 |
| WO | 2016/056663 | 4/2016 |
| WO | 2016/199717 | 12/2016 |

OTHER PUBLICATIONS

Söz et al., "Simple processes for the preparation of superhydrophobic polymer surfaces", Polymer, 2016, vol. 99, pp. 580-593.
Extended European Search Report issued Sep. 24, 2021 in corresponding European Patent Application No. 18867464.2.
International Search Report issued Dec. 18, 2018 in International (PCT) Application No. PCT/JP2018/038129.
Cho et al., "Transparent Superhydrophobic/Translucent Superamphiphobic Coatings Based on Silica-Fluoropolymer Hybrid Nanoparticles", Langmuir, 2013, vol. 29, No. 48, pp. 15051-15057.
Zhang et al., "Flexible and mechanically robust superhydrophobic silicone surfaces with stable Cassie-Baxter state", Journal of Materials Chemistry A, 2016, vol. 4, pp. 14180-14186.

* cited by examiner

*Primary Examiner* — Nathanael T Zemui
(74) *Attorney, Agent, or Firm* — Wenderoth, Lind & Ponack, L.L.P.

(57) ABSTRACT

An object, of the present invention is to provide a new liquid-repellent coating film. This object can be achieved by a coating film that has a fluorine content of less than 1 wt %, a water contact angle (droplet: 2 μL) of 115° or more, and a water contact angle of 100° or more after surface friction with a PET film (under a load of 100 gf/$cm^2$; 1500 reciprocations); and that satisfies at least one of the following regarding surface roughness indices:

(a) an average surface roughness Ra of 1.6 μm or more; and (b) a Wenzel roughness factor of 1.2 or more.

17 Claims, No Drawings

COATING FILM

TECHNICAL FIELD

The present invention relates to a coating film; in particular, to a liquid-repellent coating film.

BACKGROUND ART

Heretofore various liquid-repellent coating film have been proposed.

For example, there has been proposed a method of imparting super liquid repellency to a surface by chemically binding a fluoroalkylsilane compound to the surface to be treated, the surface having thereon a cured coating film comprising silica particles etc. (Patent Literature (PTL) 1).

As another example, a method of forming a coating film by mixing alkoxysilane, perfluoroalkylsilane, and silica particles, and hydrolyzing the alkoxysilane in such a mixed state, has been proposed (Patent Literature (PTL) 2).

As a further example, a coating film obtained by copolymerizing a fluorine-containing monomer and particles having a radically polymerizable group on the surface thereof has been proposed (Non-patent Literature (NPL) 1).

As another example, there has been proposed a coating film containing polymers having constituent units based on:

(1) at least one type of fine particle having a polymerizable group; and (2) at least one type of compound having a polymerizable group, wherein at least one type of fine particle (1) and/or at least one type of compound (2) have a fluoroalkyl group; and at least one type of compound (2) is a compound having two or more polymerizable groups in the molecule (Patent Literature (PTL) 3).

As yet another example, a mechanically robust super-water-repellent material comprising a water-repellent silica fine particle and a highly water-repellent silicone material (polydimethylsiloxane: PDMS) has been proposed (Non-patent Literature (NPL) 2).

CITATION LIST

Patent Literature

PTL 1: JP2001-131318A
PTL 2: JP2010-89373A
PTL 3: WO2016/056663

Non-Patent Literature

NPL 1: Cho et al., "Transparent superhydrophobic/translucent superamphiphobic coatings based on silica-fluoropolymer hybrid nanoparticles," Langmuir, 2013, 29 (48), pp. 15051-15057

NPL 2: Zhang et al., "Flexible and mechanically robust superhydrophobic silicone surfaces with stable Cassie-Baxter state", J. Mater. Chem. A, 2016, 4, 14180-14186

SUMMARY OF INVENTION

Technical Problem

However, the provision of another new liquid-repellent coating film is desired.

As shown in the above examples, liquid-repellent coating films heretofore known (in particular, super liquid-repellent coating films) are fluorine-containing coating films.

The present inventors aim to provide a new liquid-repellent coating film (in particular, a super liquid-repellent film) that is not a fluorine-containing coating film.

Solution to Problem

As a result of extensive research, the present inventors found that the above object can be achieved by a coating film that has a fluorine content of less than 1 wt %, a water contact angle of 115° or more, and a water contact angle of 100° or more after surface friction with a PET film (under a load of 100 g/cm$^2$, 1500 reciprocations); and that satisfies at least, one of the following regarding surface roughness indices:

(a) an average surface toughness Ra of 1.6 μm or more, and (b) a Wenzel roughness factor of 1.2 or more.

Thus, the present invention has been accomplished.

The present invention includes the following embodiments.

Item 1

A coating film having a fluorine content of less than 1 wt %, a water contact angle (droplet: 2 μL) of 115° or more, and a water contact angle of 100° or more after surface friction with a PET film (under a load of 100 gf/cm$^2$; 1500 reciprocations), and satisfying at least one of the following regarding surface roughness indices:

(a) an average surface roughness Ra of 1.6 μm or more; and (b) a Wenzel roughness factor of 1.2 or more.

Item 2

The coating film according to Item 1, wherein the average surface roughness Ra is in the range of 1.6 to 20 μm.

Item 3

The coating film according to Item 1 or 2, wherein the Wenzel roughness factor is in the range of 1.6 to 10.

Item 4

The coating film according to any one of Items 1 to 3, wherein the water contact angle is 120° or more.

Item 5

The coating film according to any one of Items 1 to 3, wherein the water contact angle is 150° or more.

Item 6

The coating film according to any one of Items 1 to 5, wherein in the surface friction with a PET film (under a load of 100 gf/cm$^2$), the number of times of surface friction that allows the coating film to maintain a water contact angle of 100° or more is 20000 reciprocations or more.

Item 7

The coating film according to any one of Items 1 to 6, wherein the coating film comprises constituent units derived from the following (A) and (B):

(A) at least one modified fine particle comprising
(i) a core fine particle and
(ii) one or more modifying moieties that modify the core fine particle, wherein at least one or all of the modifying moieties have one or more polymerizable groups (a),
and not containing fluorine; and
(B) at least one compound containing one or more polymerizable groups (b) in the molecule, and not containing fluorine, wherein at least one of the at least one compound (B) is
(Bm) a compound having two or more polymerizable groups in the molecule.

Item 8

The coating film according to Item 7, wherein one or both of the polymerizable groups (a) and (b) are radically reactive groups.

Item 9

The coating film according to Item 8, wherein one or both of the polymerizable groups (a) and (b) are a vinyl group, a (meth)acrylic group, a styryl group, or a maleimide group.

Item 10

The coating film according to any one of Items 7 to 9, wherein the core fine particle (i) has a number average primary particle size in the range of 5 to 1000 nm.

Item 11

The coating film according to any one of Items 7 to 10, wherein at least one core fine particle (i) is an inorganic particle.

Item 12

The coating film according to any one of Items 7 to 11, wherein at least one of the at least one compound (B) is (meth)acrylate.

Item 13

The coating film according to Item 12, wherein at least one of the at least one compound (B) is $C_1$-$C_{22}$ alkyl (meth)acrylate.

Item 14

The coating film according to Item 13, wherein at least one of the at least one compound (B) is $C_{16}$-$C_{22}$ alkyl (meth)acrylate.

Item 15

A composition comprising
(A) at least one modified fine particle comprising
a core fine particle and
one or more polymerizable groups (a) on the surface of the particle,
and not containing fluorine; and
(Bs) at least one compound containing one polymerizable group (b) in the molecule, and not containing fluorine.

Item 16

A composition comprising a polymer containing structural units derived from
(A) at least one modified fine particle comprising a core fine particle and one or more polymerizable groups (a) on the surface of the particle, and not containing fluorine; and
(Bs) at least one compound containing one polymerizable group (b) in the molecule, and not containing fluorine.

Item 17

The composition according to Item 16, further comprising (Bm) a compound containing two or more polymerizable groups in the molecule.

Item 18

The composition according to Item 17, wherein the compound (Bm) is present in an amount of 1 to 95 parts by mass per 100 parts by mass of the polymer.

Item 19

The composition according to Item 1 or 18, wherein the composition forms the coating film of any one of Items 1 to 14, when combined with (Bm) the compound containing two or more polymerizable groups in the molecule and cured.

Item 20

A kit comprising
(A) at least one modified fine particle comprising a core fine particle and one or more polymerizable groups (a) on the surface of the particle, and not containing fluorine; and
(Bs) at least one compound containing one or more polymerizable groups (b) in the molecule, and not containing fluorine; and further comprising
(Bm) at least one compound containing two or more polymerizable groups (b) in the molecule, and not containing fluorine, the compound (Bm) being disposed apart from the modified fine particle (A) and compound (Bs).

Item 21

An article comprising the coating film of any one of Items 1 to 14 on a part of the surface or on the entire surface of the article.

Item 21

A method for coating an article, comprising forming the coating film of any one of Items 1 to 14 on a part of the surface or on the entire surface of the article.

Item 22

A method for subjecting an article to a liquid repellent treatment, comprising forming the coating film of any one of Items 1 to 14 on a part of the surface or on the entire surface of the article.

Item 23

A method for subjecting an article to a liquid repellent treatment, comprising applying, to a part of the surface or to the entire surface of the article, (A) at least one modified fine particle comprising a core fine particle and one or more polymerizable groups (a) on the surface of the particle, and not containing fluorine; and (B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine.

Item 24

A fine particle for forming the coating film of any one of Items 1 to 14, the particle containing one or more polymerizable groups, and not containing a fluorine atom.

Item 25

A compound for forming the coating film of any one of Items 1 to 14, the compound containing one or more polymerizable groups, and not containing a fluorine atom.

Item 26

A compound for forming the coating film of any one of Items 1 to 14, the compound containing two or more polymerizable groups and not containing a fluorine atom.

Item 27

A composition for forming the coating film of any one of Items 1 to 14, comprising at least one member selected from the group consisting of:

(A) at least one modified fine particle comprising a core fine particle and one or more polymerizable groups (a) on the surface of the particle, and not containing fluorine; and (B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine.

Item 28

A coating composition comprising at least one member selected from the group consisting of:

(A) at least one modified fine particle comprising a core fine particle and one or more polymerizable groups (a) on the surface of the particle, and not containing fluorine; and (B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine.

Item 29

A composition for liquid-repellent treatment comprising at least, one member selected from the group consisting of:

(A) at least one modified fine particle comprising a core fine particle and one or more polymerizable groups (a) on the surface of the particle, and not containing fluorine; and (B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine.

Advantageous Effects of Invention

According to the present invention, a novel liquid-repellent coating film is provided. The present invention particularly provides a liquid-repellent coating film (in particular, a super liquid-repellent coating film) not containing fluorine.

DESCRIPTION OF EMBODIMENTS

1. Terms

Unless otherwise specified, the symbols and abbreviations used in this specification can be assumed to have their ordinary meanings used in the technical field to which the present invention pertains, as understood from the context of the specification.

The term "contain" or "comprise" as used herein is intended to include the meanings of "consist essentially of" and "consist of."

The step, treatment, or operation described herein can be performed at room temperature, unless otherwise specified.

The term "liquid repellency" as used herein includes water repellency, oil repellency, and a combination of water repellency and oil repellency.

The term "liquid repellency" as used herein includes super liquid repellency.

The term "super liquid repellency" as used herein includes super water repellency, super oil repellency, and a combination of super water repellency and super oil repellency.

The room temperature referred to herein can mean a temperature in the range of 10 to 30° C.

The term "$C_n$-$C_m$" (wherein n and m are numerals) as used herein indicates that the number of carbon atoms is n or more and m or less, as would be generally understood by a person skilled in the art.

The term "polymerizable group" as used herein means a group involved in a polymerization reaction.

The term "polymerization reaction" as used herein means a reaction in which two or more molecules (e.g., two molecules, or three or more molecules) are bonded to form another compound. The "two or more molecules" may be identical to or different from each other.

Examples of the "hydrocarbon group" referred to herein include, unless otherwise specified, (1) aliphatic (non-aromatic) hydrocarbon groups (e.g., benzyl) optionally substituted with one or more aromatic hydrocarbon groups, and (2) aromatic hydrocarbon groups optionally substituted with one or more aliphatic hydrocarbon groups (e.g., tolyl).

In the present specification, aromatic hydrocarbon groups are sometimes referred to as aryl groups.

The "hydrocarbon group" referred to herein can be a monovalent or higher valent group.

The hydrocarbon group referred to herein can be cyclic or acyclic (e.g., linear or branched); or a combination thereof, unless otherwise specified.

The "aliphatic hydrocarbon group" referred to herein can be an acyclic hydrocarbon group, a cyclic hydrocarbon group, or a combination thereof, unless otherwise specified.

Examples of such combinations include (1) a cyclic hydrocarbon group substituted with one or more acyclic hydrocarbon groups, and (2) an acyclic hydrocarbon group substituted with one or more cyclic hydrocarbon groups.

Examples of "aliphatic hydrocarbon groups" referred to herein include alkyl, alkenyl, alkynyl, and cycloalkyl, unless otherwise specified.

Examples of "alkyl groups" referred to herein include linear or branched alkyl groups having 1 to 30 carbon atoms, unless otherwise specified. Specific examples include methyl, ethyl, propyl (e.g., n-propyl, isopropyl), butyl (e.g., n-butyl, isobutyl, sec-butyl, tert-butyl), pentyl (e.g., n-pentyl, tert-pentyl, neopentyl, isopentyl, sec-pentyl, 3-pentyl), hexyl, heptyl, octyl, nonyl, undecyl, dodecyl, tridecyl, tetradecyl, pentadecyl, hexadecyl, heptadecyl, octadecyl, nonadecyl, icosyl, and docosyl.

Examples of "alkenyl groups" referred to herein include linear or branched alkenyl groups having 2 to 30 carbon atoms, unless otherwise specified. Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

Examples of "alkynyl groups" referred to herein include linear or branched alkynyl groups having 2 to 30 carbon atoms, unless otherwise specified. Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

Examples of "cycloalkyl groups" referred to herein include cycloalkyl groups having 3 to 8 carbon atoms, unless otherwise specified. Specific examples include cyclopentyl, cyclohexyl, and cycloheptyl.

Examples of "aromatic hydrocarbon groups" referred to herein include aromatic hydrocarbon groups having 6 to 14 carbon atoms, unless otherwise specified. Specific examples include phenyl, naphthyl, phenanthryl, anthryl, and pyrenyl.

2. Coating Film

The present invention provides a coating film that has a fluorine content of less than 1 wt %, a water contact angle (droplet: 2 μL) of 115° or more, and a water contact angle of 100° or more after surface friction with a PET film (under a load of 100 g/$cm^2$, 1500 reciprocations); and that satisfies at least one of the following regarding surface roughness indices:

(a) an average surface roughness Ra of 1.6 μm or more, and (b) a Wenzel roughness factor of 1.2 or or more.

2.1. Physical Properties of Coating Film

2.1.1. Composition of Coating Film

Preferably, the coating film of the present invention can be neither a silicone-containing coating film (e.g., a dimethylpolysiloxane-containing coating film) nor a fluorine-containing coating film. Despite not containing silicone or fluorine, the coating film of the present invention can surprisingly exhibit excellent liquid repellency (particularly water repellency).

2.1.1.1. Fluorine Content

The fluorine content of the coating film as referred to herein is defined as the content of fluorine element in an elemental composition determined by X-ray photoelectron spectroscopy (XPS) measurement.

The XPS measurement is performed using a commercially available apparatus (e.g., ESCA3400, product name, produced by Shimadzu Corporation; and PHI 5000 VersaProbe II, product name, produced by ULVAC-PHI).

The coating film has a fluorine content of less than 1 mass %, preferably less than 0.75 mass %, and more preferably less than 0.5 mass %.

The fluorine content of the entire coating film of the present invention is less than 1 mass %, preferably less than 0.75 mass %, and more preferably less than 0.5 mass %. In other words, the coating film of the present invention can be a fluorine-free coating film.

The fluorine content of the coating film of the present invention can be determined by using a fluorine content measurement method in which the detection limit of the fluorine content is 1 mass % or less.

As would be generally understood by a person skilled in the art, when no fluorine is detected by analysis using the fluorine content measurement method with a detection limit of 1 mass % or less, this means that the fluorine content is less than 1 mass %.

Examples of such methods for analyzing the fluorine content of the coating film include (1) a method comprising partially peeling the coating film from a substrate, and performing analysis; and (2) a method comprising performing analysis with the coating film being maintained in the state of coating the substrate.

Either of the above methods can be appropriately selected according to, for example, the state of the coating film to be analyzed.

The fluorine content of the coating film of the present invention determined by analytical measurement is preferably less than 1 mass %, more preferably less than 0.75 mass %, and even more preferably less than 0.5 mass %. In other words, the coating film of the present invention can be a fluorine-free coating film.

Specific examples of (1) the method comprising partially peeling the coating film from a substrate and performing analysis include a method comprising burning a sample using a flask, and performing analysis using an ion meter.

Specific examples of the method (2) of analyzing the coating film with the coating film being maintained in the state of coating the substrate include X-ray photoelectron spectroscopy, energy dispersive X-ray fluorescence analysis using a scanning electron microscope, and the like.

One of these methods can be appropriately selected according to, for example, the state of the coating film to be analyzed.

2.1.1.2. Dimethylpolysiloxane (PDMS) Content

The dimethylpolysiloxane (PDMS) content of the entire coating film of the present invention is preferably less than 1 mass %, more preferably less than 0.75 mass %, and even more preferably less than 0.5 mass %.

In other words, the coating film of the present invention can be a dimethylpolysiloxane (PDMS)-free coating film.

The PDMS content of the coating film can be determined, for example, by measurement using total reflection infrared spectroscopy (ATR-IR).

The measurement of the content by this method can be performed using a commercially available apparatus (e.g., FT-IR Nicolet 6700; product name, produced by Thermo Fisher Scientific Inc.).

The content can also be determined by measurement by time-of-flight secondary ion mass spectrometry (ToF-SIMS).

The measurement of the content by this method can be performed using a commercially available apparatus (e.g., PHI nanoTOF II; product name, produced by ULVAC-PHI Inc.).

2.1.2. Surface Roughness

The surface roughness of the coating film of the present invention satisfies at least one of the following regarding surface roughness indices:

(a) an average surface roughness Ra of 1.6 μm or more, and (b) a Wenzel roughness factor of 1.2 or more.

2.1.2.1. Average Surface Roughness Ra

In a preferred embodiment of the present invention, the coating film of the present invention has an average surface roughness Ra in the range of 1.6 μm or more, more preferably 1.6 to 20 μm, even more preferably 2.0 to 19.0 μm, and still even more preferably 2.5 to 19.0 μm.

This feature can be one of the factors that provide the coating film of the present invention with higher liquid repellency.

This feature can be one of the factors that provide the coating film of the present invention with higher durability.

The average surface roughness Ra is a numerical value measured by the following method.

Measuring Method

The average surface roughness in a quadrangular area of 527.0 μm×703.0 μm is calculated.

Specifically, the measurement is performed using a VK-9710 (trade name; produced by Keyence Corporation) color 3D laser microscope and an MUL00201 (trade name; produced by Nikon Corporation) microscope unit attached thereto; or equivalents to these.

2.1.2.2. Wenzel Roughness Factor

In a preferred embodiment of the present invention, the coating film of the present invention has a Wenzel roughness factor of 1.2 or more, more preferably in the range of 1.6 to 10, more preferably 2.4 to 9, and even more preferably 3.0 to 8.

This feature can be one of the factors that provide the coating film of the present invention with higher liquid repellency.

This feature can be one of the factors that provide the coating film of the present invention with higher durability.

The Wenzel roughness factor is herein used in its usual meaning. The Wenzel roughness factor refers to a ratio of the actual surface area of the coating film to a planar surface area (i.e., geometric surface area) of the coating film. That is, according to the definition thereof, the Wenzel roughness factor is always 1 or more.

The Wenzel roughness factor referred to herein is a numerical value obtained by the following measuring method.

Measuring Method

The actual surface area is measured in a quadrangular area of 331.5 μm×351.5 μm, and the Wenzel roughness factor is calculated.

The measurement is performed using a VK-9710 (trade name; produced by Keyence Corporation) color 3D laser microscope and a CF IC EPI Plan MUL00201 (trade name; produced by Nikon Corporation) objective lens attached thereto; or equivalents to these.

2.1.4. Water Contact Angle

The coating film of the present invention has a water contact angle of 115° or more, preferably 120° or more, more preferably 130° or more, and even more preferably 150° or more.

The water contact angle referred to herein is a static contact angle of water. The water contact angle is a numerical value obtained by the following measuring method.

Measuring Method

Using water (droplet: 2 μL), the measurement was performed at 5 points per sample using a Drop Master 701 (trade name; produced by Kyowa Interface Science, Inc.) contact angle meter, or an equivalent thereto.

When the static contact angle is 150° or more, the liquid may not be able to stand independently on the surface of the substrate. In that case, the static contact angle is measured using a syringe needle as a support, and the value obtained at that time is regarded as the static contact angle.

2.1.5. n-Hexudecane Contact Angle

The coating film of the present invention preferably has an n-hexadecane contact angle (droplet: 2 μL) of 40° or more, more preferably 50° or more, even more preferably 60° or more, and still even more preferably 70° or more.

In the present specification, n-hexadecane is sometimes abbreviated as n-HD.

The n-HD contact angle referred to herein is a static contact angle of n-HD. The n-HD contact angle is a numerical value obtained by the following measuring method.

Measuring Method

Using n-HD (droplet: 2 μL), the measurement was performed at 5 points per sample using a Drop Master 701 (trade name; produced by Kyowa Interface Science, Inc.) contact angle meter, or an equivalent thereto.

When the static contact angle is 150° or more, the liquid may not be able to stand independently on the surface of the substrate. In that case, the static contact angle is measured using a syringe needle as a support, and the value obtained at that time is regarded as the static contact angle.

2.1.6. Liquid-Repellant Abrasion Resistance of Coating Film 2.1.6.1. Water Contact Angle After Surface Friction with PET Film (Under a Load of 100 gf/cm$^2$, 1500 Reciprocations)

The water contact angle after surface friction with a PET film (under a load of 100 gf/cm$^2$, 1500 reciprocations) is 100° or more, preferably 125° or more, more preferably 120° or more, and even more preferably 150° or more.

2.1.6.2. Water Contact Angle After Surface Friction with PET Film (Under a Load of 100 gf/cm$^2$, 20000 Reciprocations)

In surface friction using a PET film (under a load of 100 gf/cm$^2$), the number of times of surface friction that allows the coating film to maintain a water contact angle of 100° or more is preferably 20000 reciprocations or more.

The contact angle is a numerical value obtained by the following measuring method.

Measuring Method

A PET film (trade name: "PET Film U-46"; produced by Toray Industries, Inc.), or an equivalent thereto, is attached to the holder of an abrasion resistance tester (trade name: "Rubbing Tester (triple series) 151E"; produced by Imoto Machinery Co., Ltd.) (area in contact with a test sample: 1 $cm^2$). The surface of a test sample is wiped by rubbing with the PET film a predetermined number of times under a load of 100 g. The water contact angle is then measured by the water contact angle measuring method described above.

2.2. One Preferred Embodiment of the Coating Film, and Composition Thereof

The coating film preferably comprises constituent units derived from (A) at least one modified fine particle comprising (i) a core fine particle and (ii) one or more modifying moieties that modify the core fine particle (wherein at least one or all of the modifying moieties have one or more polymerizable groups (a)), and not containing fluorine; and (B) at least one compound containing one or more polymerizable groups (b) in the molecule, and not containing fluorine, wherein at least one of the at least one compound (B) is (Bm) a compound having two or more polymerisable groups in the molecule.

The fluorine content is less than 1 mass %.

Among compound (B) referred to herein, a compound having one polymerizable group in the molecule is sometimes referred to as compound (Bs) in order to distinguish the compound from compound (Bm).

To explain the coating film of the present invention, embodiments of the coating film of the present invention are described below. However, the present invention is not limited thereto.

Embodiment E1

The coating film according to one embodiment of the present invention comprises

[1] a first compound containing, as constituent units, (1) a constituent unit derived from modified fine particle (A) and (2) a constituent unit derived from compound (Bs)

(wherein tho first compound can be in the form of containing a fine particle); and

[2] a second compound containing, as a constituent unit, a constituent unit derived from compound (Bm)

(wherein the second compound can have a mesh-like structure).

Just to note, the coating film according to this embodiment may contain other compounds. Examples of such other compounds include the first compound in the following embodiment E2.

Embodiment E2

The coating film according to another embodiment of the present invention comprises

[1] a first compound containing, as constituent units, (1) a constituent unit derived from modified fine particle (A) and (2) a constituent, unit derived from compound (Bm)

(wherein the first compound can have a mesh-like structure containing a fine particle); and, if desired, further comprises

[2] a second compound containing, as a constituent unit, (1) a constituent unit derived from compound (Bm)

(wherein the second compound can have a mesh-like structure).

Just to note, the coating film according to this embodiment may contain other compounds. Examples of such other compounds include the first compound in the above embodiment E1.

The coating film according to one embodiment of the present invention preferably has a surfactant content of 1 mass % or less.

The "surfactant" as referred to herein means an organic compound having a hydrophobic part and a hydrophilic part, and having surfactant activity. The "organic compound" as referred to herein means a compound containing at least carbon and hydrogen as constituent atoms, and containing metal and/or metalloid atoms in a proportion of less than 50% in terms of atomicity.

In the present specification, the "metalloid atoms" refer to boron, silicon, germanium, arsenic, antimony, and tellurium.

2.2.1. Modified Fine Particle (A)

The modified fine particle (A) contains (i) a core fine particle, and (ii) one or more modifying moieties that modify the core fine particle.

The mode in which the modifying moiety is bound to the surface of the fine particle is not particularly limited. Examples include covalent, bonding, coordination bonding, ionic bonding, hydrogen bonding, and bonding by Van der Waals force.

In the coating film of the present invention, the core fine particle preferably has a number average particle size in the range of 5 to 1000 nm.

In the coating film of the present invention, at least one core fine particle (i) is an inorganic particle.

In at least one or all of the one or more modifying moieties, the proportion of the polymerizable groups (a) to the modifying moiety having one or more polymerizable groups (a) can be, for example, 10 mol % or more, 30 mol % or more, 50 mol % or more, 70 mol % or more, 90 mol % or more, 95 mol % or more, or 100 mol %.

The number of modifying moieties on the core fine particle (i) of the modified fine particle (A) can be, for example, 1 or more, 2 or more, 3 or more, 5 or more, 7 or more, 10 or more, 15 or more, 30 or more, 50 or more, 70 or more, or 100 or more.

The number of polymerizable groups on the core fine particle (i) of the modified fine particle (A) can be 1 or more, 2 or more, 3 or more, 5 or more, or more, 10 or more, 15 or more, 30 or more, 50 or more, 70 or more, or 100 or more.

2.2.1.1. Core Fine Particle (i)

Examples of the core fine particle (i) of the modified fine particle (A) include inorganic fine particles (e.g., silica fine particles, such as porous silica fine particles, and metal oxide fine particles); organic fine particles (e.g., carbon black, fullerene, and carbon nanotubes); and combinations of inorganic fine particles and organic fine particles (e.g., a mixture of two or more types of fine particles).

This feature can be one of the factors that provide the coating film of the present invention with higher liquid repellency.

This feature can be one of the factors that provide the coating of the present invention with higher durability.

The core fine particle (i) used in the present invention preferably has a number average particle size in the range of 0.5 nm to 1000 nm, more preferably 1 nm to 500 nm, and even more preferably 5 nm to 300 nm.

When the core fine particle (i) has a number average particle size within the range described above, the parameters regarding the water contact angle, average surface roughness, and Wenzel roughness factor described above can be more easily achieved.

Some or all of the primary particles of the modified fine particle (A) and core fine particle (i) may be aggregated to form a secondary particle in the coating film of the present invention.

The number average particle size can be a number average particle size of particles including the secondary particle and the primary particle (which is a primary particle not in the form of a secondary particle).

The number average particle size of the core fine particle (i) can be measured by the following method.

Measuring Method

After samples are photographed with a transmission electron microscope or a scanning electron microscope, the diameter of 200 particles or more is measured on the photographs, and the arithmetic average value is calculated.

This feature can be one of the factors that provide the coating film of the present invention with higher liquid repellency.

This feature can be one of the factors that provide the coating film of the present invention with higher durability.

When the core fine particle (i) used in the present invention is a porous silica fine particle, the core fine particle (i) in a dry powder state preferably has an apparent density of 0.01 to 0.5 g/cm$^3$, more preferably 0.015 to 0.3 g/cm$^3$, and even more preferably 0.02 to 0.05 g/m$^3$.

When the porous silica fine particle has an apparent density within the range described above, the parameters regarding the water contact angle, average surface roughness, and Wenzel roughness factor described above can be more easily achieved.

The apparent density can be measured by the following method.

Measuring Method

After 0.2 g of a powder sample is placed in a 10-ml measuring cylinder, the volume is measured. The obtained density is defined as apparent density.

2.2.1.2. Polymerizable Group (a) Contained in Modifying Moiety (ii)

Examples of polymerizable group (a) include radically polymerizable groups, cationic polymerizable groups, and anionic polymerizable groups.

Preferable examples include radically polymerizable groups.

Examples of radically polymerizable groups include a vinyl group, (meth)acrylic groups, a styryl group, and a maleimide group; and groups containing these groups.

Preferable examples include (meth)acrylic groups and a styryl group; and groups containing these groups.

The polymerizable group (ii) can be disposed in a polymerizable state at at least one end of the modified moieties.

Examples of the modifying moieties having one or more polymerizable groups (ii) include an alkyl group substituted with one or more polymerizable groups described above (e.g., alkyl groups having 1 to 10 carbon atoms), and a polyether group substituted with one or more polymerizable groups (e.g., polyether groups having 2 to 10 carbon atoms).

This feature can be one of the factors that provide the coating film of the present invention with higher liquid repellency.

This feature can be one of the factors that provide the coating film of the present invention with higher durability.

The modified fine particle (A) does not contain fluorine.

The phrase "not containing fluorine" referred to herein includes substantially not containing fluorine. Specifically, not containing fluorine can mean that the fluorine content is less than 1 wt %.

The modified fine particle (A) can be used singly, or in a combination of two or more.

2.2.1.3. Method for Producing Modified Fine Particle (A)

The modified fine particle (A) can be produced by using a known method or a method similar thereto, and appropriately selecting a binding mode as described above.

Examples of usable methods include a method comprising allowing a compound containing (a) one or more polymerizable groups and (b) one or more moieties having reactivity with the particle surface to react with the core fine particle (i)).

Here, the one or more moieties (b) having reactivity with the particle surface can be appropriately selected according to the chemical structure or the state of the surface of the core fine particle (i).

Examples of such reactions include silane coupling.

Specific examples of the method include (1) a method comprising allowing a hydroxyl group or a silanol group on the silica fine particle to be bound to a functional group in a compound that is to be a modifying moiety (e.g., a method using silane coupling);

(2) a method comprising allowing a metal oxide on the metal particle to be bound to a phosphonic acid moiety in a compound that is to be a modifying moiety; and (3) a method comprising allowing gold of metal particles containing gold to be bound to a thiol moiety of a compound that is to be a modifying moiety.

2.2.2. Compound (B)

In the present invention, compound (B), which contains one or more polymerizable groups (b) in the molecule and does not contain fluorine, can be used singly, or in a combination of two or more.

Among compound (B), at least one compound (B) is a compound containing two or more polymerizable groups in the molecule (compound (Bm)).

Examples of polymerizable group (b) include examples of the polymerizable group (a) described above.

At least, one compound (B) in the coating film of the present invention is preferably (meth)acrylate.

When compound (B) includes (meth)acrylate, the parameters regarding the water contact angle, average surface roughness, and Wenzel roughness factor described above can be more easily achieved.

At least one compound (B) in the coating film of the present invention is preferably $C_1$-$C_{22}$ alkyl (meth)acrylate, more preferably $C_{16}$-$C_{22}$ alkyl (meth)acrylate, and even more preferably $C_{18}$-$C_{22}$ alkyl (meth)acrylate.

The alkyl in compound (B) is preferably linear.

More preferably, all of compounds (B) in the coating film of the present invention are $C_1$-$C_{22}$ alkyl (meth)acrylate, more preferably $C_{16}$-$C_{22}$ alkyl (meth)acrylate, and even more preferably $C_{18}$-$C_{22}$ alkyl (meth)acrylate.

The (meth)acrylate content of the coating film of the present invention is preferably 33.5 mass %, or more, and more preferably 50.0 mass % or more, based on the entire coating film.

This feature can be one of the factors that provide the coating film of the present invention with higher liquid repellency.

This feature can be one of the factors that provide the coating film of the present invention with higher durability.

2.2.2.1. Compound Having Two or More Polymerizable Groups in the Molecule (Compound (Bm))

The compound having two or more polymerizable groups in the molecule (compound (Bm)) (also referred to as a polyfunctional polymerizable compound or polyfunctional crosslinkable compound) is preferably a compound containing 2 to 8 polymerizable groups (b), more preferably 3 to 6 polymerizable groups (b), and even more preferably 3 polymerizable groups (b), in the molecule, in view of abrasion resistance of the coating film of the present invention.

The compound (Bm) is preferably a three-dimensionally crosslinkable compound.

"Three-dimensionally crosslinkable" means that the compound can form a three-dimensional structure by a polymerization reaction.

When a three-dimensionally crosslinkable compound is used as compound (Bm), the parameter regarding the water contact angle after surface friction with a PET film (under a load of 100 gf/cm$^2$; 1500 reciprocations) can be more easily achieved.

The polymerizable group (b) is preferably capable of binding to the modified fine particle (A).

When a group capable of binding to the modified fine particle (A) is used as polymerizable group (b), the parameter regarding the water contact after surface friction with a PET film (under a load of 100 gf/cm$^2$, 1500 reciprocations) can be more easily achieved.

Examples of polymerizable group (b) include radical polymerizable groups, cationic polymerizable groups, and anionic polymerizable groups.

Particularly preferred examples of polymerizable group (b) include radical polymerizable groups. Radical polymerizable groups are preferable in terms of versatility and/or reactivity.

The polymerizable group (a) and polymerizable group (b) of modified fine particle (A) are preferably groups that react on the same principle.

Examples of preferred embodiments include an embodiment in which the polymerizable group (a) is a radically polymerizable group, and the polymerizable group (b) is also a radically polymerizable group.

Examples of radical polymerizable groups include a vinyl group, a (meth)acrylic group, a styryl group, and a maleimide group.

Preferable examples of radical polymerizable groups include (meth)acrylic groups and a styryl group. These radical polymerizable groups are preferable in view of versatility and/or reactivity.

Examples of compound (Bm) include a compound represented by the following formula (Bm−1).

(Bm-1)

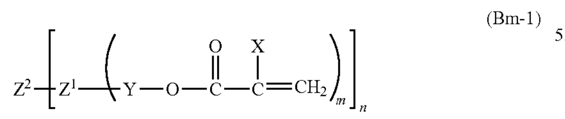

(wherein X is a hydrogen atom, a chlorine atom, a bromine atom, an iodine atom, a $CX_3$ group (wherein X, in each occurrence, is the same or different, and represents a hydrogen atom or a chlorine atom), a cyano group, a $C_1$-$C_{21}$ linear or branched alkyl group, a substituted or unsubstituted benzyl group, a substituted or unsubstituted phenyl group, or a $C_1$-$C_{20}$ linear or branched alkyl group;

Y represents a direct bond, a $C_1$-$C_{10}$ hydrocarbon group optionally having an oxygen atom, a $—CH_2CH_2N(R^1)SO_2$ group (wherein $R^1$ represents 1 to 4 carbon atoms; the right end of the formula is bound to $Z^1$, and the left end of the formula is bound to O);

a $—CH_2CH(OY_1)CH_2$ group (wherein $Y^1$ is a hydrogen atom or an acetyl group; the right end of the formula is bound to $Z^1$, and the left, end of the formula is bound to O), or a $—(CH_2)_nSO_2—$ group (wherein n is 1 to 10; the right end of the formula is bound to $Z^1$; and the left end of the formula is bound to O);

$Z^1$, in each occurrence, is the same or different, and represents a hydrocarbon group having a valency of m+1 (wherein the hydrocarbon group may contain one or more oxygen atoms), a carbon atom, or an oxygen atom;

$Z^2$, in each occurrence, is the same or different, and represents a hydrocarbon group having a valency of n (wherein the hydrocarbon group optionally contains one or more oxygen atoms), a carbon atom, or an oxygen atom;

m is an integer from 1 to 3;

n is an integer of 1 to 4 (preferably 2 to 4); and the product of m and n is 2 or more (preferably 2 to 4).

In formula (Bm−1), the hydrocarbon of $Z^1$ and $Z^2$ can be cyclic or acyclic, and can be linear or branched.

In formula (Bm−1), the hydrocarbon of $Z^1$ and $Z^2$ is preferably a $C_1$-$C_{10}$, more preferably $C_1$-$C_6$, and even more preferably $C_1$-$C_2$ hydrocarbon.

Specific examples of the compound represented by the above formula (Bm−1) include the following compounds:

$CH_3—CH_2—C—(CH_2OCO—CH{=}CH_2)_3$ (trimethylolpropane triacrylate, TMPTA);

$C(—CH_2OCO—CH{=}CH_2)_4$; and $O[—CH_2(—CH_2OCO—CH{=}CH_2)_3]_2$.

The coating film of the present invention has the above-described various physical properties, which can be obtained by copolymerization using the modified fine particle (A) and the compound (Bm).

This (in particular, physical properties regarding structural characteristics) can relate to excellent abrasion resistance of the coating film of the present invention.

The quantitative ratio of compound (Bm) to modified fine particle (A) can be appropriately adjusted within a range that does not significantly impair the effect of the present invention.

Specifically, the amount of compound (Bm) to be used is usually in the range of 5 to 1000 parts by weight, preferably 10 to 750 parts by weight, and more preferably 20 to 500 parts by weight, based on 100 parts by weight of the fine particle.

The compound (Bm) can be used singly, or in a combination of two or more.

2.2.2.2. Compound Having One Polymerizable Group in the Molecule (Compound (Bs))

In the production of the coating film of the present invention, in addition to modified fine particle (A) and compound (Bm), at least one compound having one polymerizable group in the molecule (compound (Bs)) (also referred to as a monofunctional polymerizable compound) can be further copolymerized.

Examples of polymerizable groups include radical polymerizable groups, cationic polymerizable groups, and anionic polymerizable groups.

Particularly preferable examples of polymerizable groups include radical polymerizable groups. Radical polymerizable groups are preferable in terms of versatility and/or reactivity.

Examples of radical polymerizable groups include a vinyl group, (math)acrylic groups, a styryl group, and a maleimide group; and the like.

Preferred examples of radical polymerizable groups include (meth)acrylic groups, a styryl group, and the like in terms of versatility and/or reactivity.

Examples of compound (Bs) include compounds represented by the following formula (Bs-1).

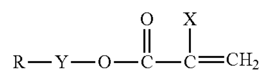

(Bs-1)

In the formula, X is hydrogen, chlorine, bromine, iodine, $—CX_3$ (wherein X, in each occurrence, is the same or different, and represents hydrogen or chlorine), cyano, a linear or branched $C_1$-$C_{21}$ alkyl group, a substituted or unsubstituted benzyl group, a substituted or unsubstituted phenyl group, or a linear or branched $C_1$-$C_{20}$ alkyl group;

Y is a single bond, a $C_1$-$C_{10}$ hydrocarbon group optionally having an oxygen atom, $—CH_2CH_2—N(—R^{ya})—SO_2—$ (wherein $R^{ya}$ is a $C_1$-$C_4$ alkyl group, the right end of the formula is bound to R, and the left end of the formula is bound to O), $—CH_2CH(—OR^{yb})—CH_2—$ (wherein $R^{yb}$ represents hydrogen or acetyl, the right end of the formula is bound to R, and the left end of the formula is bound to O), or $—(CH_2)_n—SO_2—$ (wherein n is 1 to 10, the right end of the formula is bound to R, and the left end of the formula is bound to O); and R is a hydrocarbon group optionally having one or more oxygen atoms), In formula (Bs-1), the hydrocarbon group can be cyclic or acyclic, and can be linear or branched.

In formula (Bs-1), the hydrocarbon group is preferably a hydrocarbon group having 1 to 22 carbon atoms, more preferably 16 to 22 carbon atoms, and even more preferably 13 to 22 carbon atoms.

Specific examples of compounds represented by the above formula (Bs-1) include the following compounds:

$CH_3O—CO—C(—CH_3)=CH_2$ (methyl methacrylate),
$C_2H_5O—CO—C(—CH_3)=CH_2$ (ethyl methacrylate),
$C_3H_7O—CO—C(—CH_3)=CH_2$ (propyl methacrylate),
$C_4H_9O—CO—C(—CH_3)=CH_2$ (butyl methacrylate),
$C_6H_{13}O—CO—C(—CH_3)=CH_2$ (hexyl methacrylate),
$C_8H_{17}O—CO—C(—CH_3)=CH_2$ (octyl methacrylate),
$C_{12}H_{25}O—CO—C(—CH_3)=CH_2$ (lauryl methacrylate),
$CH_3O—CO—CH=CH_2$ (methyl acrylate),
$C_2H_5O—CO—CH=CH_2$ (ethyl acrylate),
$C_3H_7O—CO—CH=CH_2$ (propyl acrylate),
$C_4H_9O—CO—CH=CH_2$ (butyl acrylate),
$C_6H_{13}O—CO—CH=CH_2$ (hexyl acrylate),
$C_8H_{17}O—CO—CH=CH_2$ (octyl acrylate),
$C_{12}H_{25}—O—CO—CH=CH_2$ (lauryl acrylate),
$C_{18}H_{37}O—CO—CH=CH_2$ (stearyl acrylate),
$C_{22}H_{45}O—CO—CH=CH_2$ (benzyl acrylate)

Compound (Bs) can be used singly, or in a combination of two or more.

The quantitative ratio of compound (Bs) (a monofunctional polymerizable compound) to compound (Bm) (a polyfunctional polymerizable compound) can be appropriately adjusted within the range that does not significantly impair the effect of the present invention.

Specifically, the compound (Bs) can be usually used in an amount of 5 to 1000 parts by weight, preferably 10 to 500 parts by weight, and more preferably 20 to 300 parts by weight, per 100 parts by weight of the compound (Bm).

2.2.3. Object to which the Coating Film is Applied

The material to which the coating film of the present invention is applied is not particularly limited. Examples include glass, resins (e.g., natural resins and synthetic resins), metals (e.g., simple metals, such as aluminum, copper, and iron, and composites such as alloys), ceramics, semiconductors (e.g., silicon, germanium), fibers, furs, leathers, woods, porcelain, stones, and building components.

The form of the material to which the coating film of the present invention is to be applied is not particularly limited.

Examples of the form of the material include main plates, films, or other forms.

For example, when the material is a fiber, the fiber may be in the form of a woven fabric or a non-woven fabric.

2.2.4. Method of Producing the Coating Film

A method for producing the coating film is described.

The coating film of the present invention can be obtained by curing a curable component contained in a composition containing the modified fine particle (A) and the compound (B) (for example, the composition of the present invention described below) on the surface to be treated.

That is, as described above, one preferred embodiment of the coating film of the present invention is a coating film comprising constituent units derived from:

(A) at least one modified fine particle comprising
 (i) a core fine particle and
 (ii) one on more modifying moieties that modify the core fine particle (wherein at least one or all of the one or more modifying moieties have at least one polymerizable group (a)), and not containing fluorine;

(B) at least one compound containing one or more polymerizable groups (b) in the molecule, and not containing fluorine, wherein at least one of the at least one compound (B) is a compound (Bm) containing at least two polymerizable groups in the molecule.

The curable component can be cured, for example, by a polymerization reaction of a polymerizable compound as the curable component.

Compound (Bm) can suitably function as the curable component or polymerizable compound.

The coating film of the present invention can be produced, for example, by one embodiment, of a method for producing a coating film described below, or a method similar thereto.

One embodiment of the method for producing a coating film according to the present invention comprises (1) a step of allowing one or more compounds (Bs) to bind to modified fine particle (A) to obtain fine particle ($A^b$) having at least one polymerizable group (a);

(2) a step of applying a composition containing fine particle ($A^b$) obtained in the step (1) and compound (Bm) to a surface to be treated; and (3) a step of polymerizing compound (Bm).

As a modification of one embodiment of the method for producing a coating film of the present invention, compound (Bm) can be used in place of at least one or all of the one or more compounds (Bs).

In this case, step (1) may be performed on the surface to be treated.

Step (2) may be performed simultaneously with Step (1) on the surface to be treated.

The reaction conditions in step (1) may be set based on common technical knowledge in accordance with the type of polymerizable group (a) on modified fine particle (A), and the type of compound (Bs) (that is, the type of binding reaction).

The application or coating of the composition to the surface to be treated in step (2) can be performed by using a known application or coating method (e.g., brushing, spraying, spin coating, bar coating, and a method using a dispenser).

If necessary, various primer treatments can be performed on the surface to be treated beforehand in order to facilitate the application.

Among these, application by spraying or bar coating is preferable. In particular, application by spraying is particularly preferable because the parameters regarding the water contact angle, average surface roughness, and Wenzel roughness factor described above can be more easily achieved.

In step (3), the coating film of the present invention can be produced by bringing the composition into contact with an object to be treated, and then curing a curable component by a polymerization reaction.

Compound (Bm) can form a coating film as described above.

Some or ail of modified fine particle (A) may be chemically bound to the coating film.

The modified fine particle (A) chemically bonded to the coating film can be chemically retained in the coating film as a part of the coating film. This contributes to the coating film having the physical properties described above.

On the other hand, the modified fine particle (A) chemically bound to the coating film can be physically (i.e., non-chemically) retained in the coating film as a part of the coating film. This contribute to the coating film having the physical properties described above.

When the composition is cured by a polymerisation reaction, the polymerization reaction can be performed in the presence or absence of a polymerization initiator.

When the compound represented by formula (2) is used, a polymerization initiator is preferably used.

Examples of preferable polymerization initiators include polymerization initiators that generate radicals or cations upon irradiation with electromagnetic waves in the wavelength range of 350 nm or less (e.g., ultraviolet rays, electron beams, X-rays, or γ-rays), and that function as a catalyst that initiates curing (a crosslinking reaction) of a carbon-carbon bond of a polymer. In general, a polymerization initiator that generates radicals or cations upon irradiation with ultraviolet rays can be used. In particular, a polymerization initiator that generates radicals upon irradiation with ultraviolet rays can be used.

Examples of the polymerization initiator include the following compounds:

Acetophenone-based polymerization initiators: acetophenone, chloroacetophenone, diethoxyacetophenone, hydroxyacetophenone, α-aminoacetophenone, hydroxypropiophenone, 2-methyl-1-[4-(methylthio)phenyl]-2-morpholinepropane-1-one, and the like;

Benzoin-based polymerization initiators: benzoin, benzoin methyl ether, benzoin ethyl ether, benzoin isopropyl ether, benzoin isobutyl ether, benzyl dimethyl ketal, and the like;

Benzophenone-based polymerization initiators: benzophenone, benzoylbenzoic acid, methyl benzoyl benzoate, 4-phenylbenzophenone, hydroxybenzophenone, hydroxypropylbenzophenone, acrylated benzophenone, Michler's ketone, and the like;

2,2-Dimethoxy-1,2-diphenylethan-1-one, 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2-methyl-1-(4-methylthiophenyl)-2-morpholinopropan-1-one, and 2-benzyl-2-dimethylamino-1-(4-morpholinophenyl)-butanone-1,2-(dimethylamino)-2-[(4-methylphenyl) methyl]-1-[4-(4-morpholinyl)phenyl]-1-butanone;

Thioxanthone-based polymerization initiators: thioxanthone, chlorothioxanthone, methylthioxanthone, diethylthioxanthone, dimethylthioxanthone, and the like.

Others: benzyl, α-acyloxime ester, acylphosphine oxide, glyoxy ester, 3-ketocoumarin, 2-ethylanthraquinone, camphorquinone, anthraquinone, and the like.

In addition to the initiators that generate radicals by light energy, such as electromagnetic waves described above, polymerization initiators that generate radicals by heat energy can also be used.

The polymerization initiators that generate radicals by heat energy can be known polymerization initiators for a thermal radical polymerization reaction.

Examples include azo-based initiators, such as azobisisobutyronitrile, methyl azoisobutyrate, and azobisdimethylvaleronitrile; and other initiators, such as benzoyl peroxide, potassium persulfate, ammonium persulfate, benzophenone derivatives, phosphine oxide derivatives, benzoketone derivatives, phenylthioether derivatives, azide derivatives, diazo derivatives, and disulfide derivatives.

These polymerization initiators can be used singly, or in a combination of two or more.

The amount of the polymerization initiator used is not particularly limited. In general, the amount of the polymerization initiator is preferably about 0.01 to 10 parts by weight, and more preferably about 3 to 7 parts by weight, per 100 parts by weight of the monomer component.

Examples of the polymerization method that can be performed in the absence of a polymerization initiator include methods of polymerization using heat, electron beams, γ-rays, etc.

Specifically, for example, the polymerization can be performed using heat and/or electromagnetic waves in the wavelength region of 350 nm or less (e.g., ultraviolet rays, electron beams, X-rays, and γ-rays).

The polymerization reaction can be performed by dividing the reaction into two or more stages.

In this case, for example, at least one compound (Bm) is preferably polymerized on the object to be treated at the final stage of the two or more stages. Specifically, after the fine particle (A) and compound (Bs) are polymerized, polymerization using compound (Bm) can be performed.

The polymerization conditions, such as polymerization temperature and polymerization time, can be appropriately adjusted according to the type and amount of monomer component used, the type and amount of polymerization initiator used, and the like. The polymerization reaction can be usually performed at a temperature of about 50 to 100° C. for 4 to 10 hours.

The coating film of the present invention can be produced by bringing the composition into contact with the object to be treated, and then curing the curable component.

When the composition comprises (1) a modified fine particle (A), and (2) a compound (Bmi) containing an isocyanate group as a polyfunctional crosslinkable compound (Bm) that is a curable component, the coating film of the present invention can be produced by preparing the modified fine particle (A), then preparing a solution in which the modified fine particle (A) and compound (Bmi) containing an isocyanate group are present together; and spreading the solution over the object to be treated.

When the composition is cured using the modified fine particle (A) and compound (Bmi), heat is preferably applied.

The heating time can be set to an appropriate time.

The reaction temperature is preferably, for example, 30° C. to 300° C., and more preferably 40° C. to 270° C.

The reaction time is, for example, preferably 1 second to 2 hours, and more preferably 5 seconds to 1 hour 30 minutes.

To form a coating film with higher durability, it is preferable that before treatment with the composition, the substrate is preferably washed with a solvent, such as acetone, isopropyl alcohol (IPA), hydrofluoroether, or a mixed solvent thereof, to remove contaminants from the surface of the substrate; and then dried.

Further, for silicon substrates or metal substrates, in addition to the above washing, chemical cleaning using an acid (e.g., hydrochloric acid, nitric acid, and hydrogen fluoride), UV ozone, etc.; or physical cleaning using sandblasting, glass beads, plasma, etc., is also useful to improve durability.

More preferably, in view of enhancing abrasion resistance, the surface is modified with a compound capable of being chemically adsorbed onto the washed substrate, and having in its structure a site capable of chemically reacting with the composition.

In the polymerization reaction, if necessary, a catalyst activator for the reaction between a hydroxyl group and an isocyanate group can be further used.

In particular, when the compound (Bmi) is used as a polyfunctional crosslinkable compound, such a catalyst is preferably used.

Examples include organic titanium compounds (e.g., titanium tetra-2-ethylhexoxide and titanium diisopropoxybis (ethyl acetoacetate)); and organic zirconia compounds (e.g., zirconium tetraacetylacatonate and zirconium dibutoxybis(ethylacetoacetate)).

These compounds are commercially available. Examples include Orgatix TA-30 (Matsumoto Fine Chemical Co., Ltd.), TC-750 (Matsumoto Fine Chemical Co., Ltd.), ZC-580 (Matsumoto Fine Chemical Co., Ltd.), and ZC-700 (Matsumoto Fine Chemical Co., Ltd.).

The polymerization reaction is preferably performed in the presence of a solvent. Examples of the solvent include ketone solvents (e.g., methyl ethyl ketone (MEK), methyl isobutyl ketone (MIBK), acetone, diethyl ketone, and dipropyl ketone);

ester solvents (e.g., ethyl acetate, methyl acetate, propyl acetate, butyl acetate, and ethyl lactate);

ether solvents (e.g., tetrahydrofuran, methyltetrahydrofuran, dioxane); and amide solvents (e.g., dimethyl formamide (DMF) and dimethylacetamide).

These solvents can be used singly, or in a combination of two or more.

Examples of such solvents include alcohol solvents such as methanol and ethanol;

non-aromatic hydrocarbon solvents such as pentane, hexane, heptane, octane, cyclohexane, decahydronaphthalene, n-decane, isododecane, and tridecane;

aromatic hydrocarbon solvents such as benzene, toluene, xylene, tetralin, veratrol, diethylbenzene, methylnaphthalene, nitrobenzene, o-nitrotoluene, mesitylene, indene, and diphenyl sulfide;

ketones such as acetone, methyl ethyl ketone, methyl isobutyl ketone, acetophenone, propiophenone, diisobutyl ketone, and isophorone;

halogenated hydrocarbon solvents such as dichloromethane, chloroform, and chlorobenzene;

ether solvents such as diethyl ether, tetrahydrofuran, diisopropyl ether, methyl t-butyl ether, dioxane, dimethoxyethane, diglyme, phenetole, 1,1-dimethoxycyclohexane, and diisoamyl ether;

ester solvents such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone;

nitrile solvents such as acetonitrile and benzonitrile;

sulfoxide solvents such as dimethyl sulfoxide and sulfolane; and amide solvents such as N,N-dimethylformamide, N,N-dimethylacetamide, N-methylpyrrolidone, 1,3-dimethyl-2-imidazolidinone, N,N-dimethylacrylamide, N,N-dimethyl acetoacetamide, N,N-diethylformamide, and N,N-diethyl acetamide; and a combination of two or more of these solvents.

The amount of solvent can be appropriately determined to allow the reaction to proceed appropriately, based on common technical knowledge.

3. Composition

The present invention further provides a composition comprising (A) at least one modified fine particle containing a core fine particle and one or more polymerizable groups (a) on the surface of the particle, and not containing fluorine; and (Bs) at least one compound containing one polymerizable group (b) in the molecule, and not containing fluorine.

The present, invention further provides a composition comprising (A) a constituent unit derived from at least one modified fine particle comprising a core fine particle and one or more polymerizable groups (a) on the surface of the particle, and not containing fluorine; and (Bs) a constituent unit derived from at least, one compound containing one polymerizable group (b) in the molecule, and not containing fluorine.

The composition according to one embodiment further contains (Bm) a compound containing two or more polymerizable groups in the molecule.

The composition preferably contains compound (Bm) in an amount of 1 to 95 parts by mass, based on 100 parts by mass of the polymer. The amount of compound (Bm) is preferably 5 to 50 parts by mass, and particularly preferably 10 to 30 parts by mass.

In the present invention, the quantitative ratio of modified fine particle (A) to compound (Bs) is preferably in the range of 1:0.1 to 1:20, more preferably 1:0.2 to 1:15, and still more preferably 1:0.5 to 1:5.

In the present invention, the quantitative ratio of modified fine particle (A) to compound (Bm) is preferably in the range of 1:0.03 to 1:2.85, more preferably 1:0.10 to 1:2.5, and more preferably 1:0.30 to 1:2.

In the present invention, the quantitative ratio of modified fine particle (Bm) to compound (Bs) is preferably in the range of 1:20 to 1:0.75, more preferably 1:15 to 1:1, and even more preferably 1:10 to 1:2.

The composition according to a preferred embodiment of the present invention is a composition that forms the coating film of the present invention, when combined with compound (Bm) having two or more polymerizable groups in the molecule and cured.

The details of the composition of the present invention can be understood by persons skilled in the art from the above description of the coating film and common technical knowledge.

Therefore, it can be understood that the composition can contain substances other than those mentioned above in the description of the coating film.

4. Kit

The present invention provides a kit comprising (A) at least one modified fine particle containing a core fine particle and one or more polymerizable groups (a) on the surface of the particle, and not containing fluorine; and (Bs) at least one compound containing one polymerizable group (b) in the molecule, and not containing fluorine; and further comprising (Bm) at least one compound containing two or more polymerizable group (b) in the molecule, and not containing fluorine, the compound (Bm) being disposed apart from the modified fine particle (A) and compound (Bs).

The details of the kit of the present invention can be understood by persons skilled in the art from the above description of the coating film and common general technical knowledge.

Therefore, it can be understood that the kit may contain substances other than those mentioned above in the description of the coating film.

The kit of the present invention can appropriately contain such substances in a mixed state, or in a state in which they are separated from each other.

5. Article

The present invention also provides an article having the coating film of the present invention on a part of the surface or on the entire surface of the article.

The details or the article of the present invention can be understood by persons skilled in the art from the above description of the coating film and common technical knowledge.

6. Method for Coating Article

The present invention also provides a method for coating an article, comprising the step of forming the coating film of the present invention on a part of the surface or on the entire surface of the article.

The details of the method for coating the article according to the present invention can be understood by persons skilled in the art from the above description of the coating film and common technical knowledge.

7. Method of Subjecting Article to Liquid Repellent Treatment

The present invention further provides a method of subjecting an article to a liquid repellent treatment, the method comprising the step of forming the coating film according to any one of claims 1 to 15 on a part of the surface or on the entire surface of the article.

The details of the method of subjecting an article to a liquid repellent treatment according to the present invention can be understood by persons skilled in the art from the above description of the coating film and common technical knowledge.

The present invention further provides a method of subjecting an article to a liquid repellent treatment, the method comprising the step of applying, to a part of the surface or to the entire surface of the article, (A) at least one modified fine particle comprising a core fine particle and one or more polymerizable groups (a) on the surface of the particle, and not containing fluorine and (B) at least one compound containing one or more polymerizable groups (b) in the molecule, and not containing fluorine; or a reaction product of particle (A) and compound (B); and (Bm) at least one compound containing one or more polymerizable groups (b) in the molecule, and not containing fluorine.

The details of the method of subjecting an article to a liquid repellent treatment can be understood by persons skilled in the art from the above description of the coating film and common technical knowledge.

8. Fine Particles for Forming Coating Film

The present invention further provides a fine particle for forming the coating film of the present invention, the fine particle containing one or more polymerizable groups, and not containing a fluorine atom.

The details of the fine particle of the article of the present invention can be understood by persons skilled in the art from the above description of the coating film and common technical knowledge.

9. Compound for Forming Coating Film

The present invention provides a compound for forming the coating film of the present invention, the compound containing one or more polymerizable groups, and not containing a fluorine atom.

The present invention further provides a compound for forming the coating film of the present invention, the compound containing two or more polymerizable groups, and not containing a fluorine atom.

The details of these compounds for forming the coating film of the present invention can be understood by persons skilled in the art from the above description of the coating film and common technical knowledge.

10. Composition for Forming Coating Film

The present invention provides a composition for forming the coating film of the present invention, the composition comprising at least one member selected from the group consisting on:

(A) at least one modified fine particle comprising a core fine particle, and one or more polymerizable groups (a) on the surface of the particle, and not containing fluorine; and (B) at least one compound containing one or more polymerizable groups (b) in the molecule, and not containing fluorine; or a reaction product of the fine particle (A) and the compound (B); and (Bm) at least one compound containing two or more polymerizable groups (b) in the molecule, and not containing fluorine.

11. Coating Composition

The present invention further provides a coating composition comprising at least one member selected from the group consisting of:

(A) at least one modified fine particle containing a core fine particle and one or more polymerizable groups (a) on the surface of the particle, and not containing fluorine; and (B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine.

The details of the liquid repellent, treatment composition of the present invention can be understood by persons skilled in the art from the above description of the coating film and common technical knowledge.

12. Composition for Liquid Repellent Treatment

The present invention further provides a composition for liquid repellent treatment, the composition comprising at least one member selected from, the group consisting of:

(A) at least one modified fine particle containing a core fine particle and one or more polymerizable groups (a) on the surface of the particle, and not containing fluorine; and (B) at least one compound containing one or more polymerizable groups (b) in the molecule and not containing fluorine; or a reaction product of particle (A) and compound (B); and (Bm) at least one compound containing two or more polymerizable groups (b) in the molecule, and not containing fluorine.

The details of the composition for liquid repellent treatment according to the present invention can be understood by persons skilled in the art from the above description of the coating film and common technical knowledge.

13. Composition

The present invention also provides a composition comprising:

(A) at least one modified fine particle containing a core fine particle and one or more polymerizable groups (a) on the surface of the particle, and not containing fluorine;

(B) at least one compound containing one or more polymerizable groups (b) in the molecule, and not containing fluorine; or a reaction product of particle (A) and compound (B); and (Bm) at least one compound containing two or more polymerizable groups (b) in the molecule, and not containing fluorine; and containing a surfactant in an amount of 10 mass % or less (preferably 5 mass % or less, 4 mass % or less, 3 mass % or less, 2 mass % or less, or 1 mass % or less);

wherein the compound (A), compound (B), and compound (Bm) are in the state of being dissolved or dispersed in the liquid medium.

The details of the composition can be understood by persons skilled in the art from the description of the present specification and common technical knowledge.

Examples of the liquid medium can be the same as the examples of solvents mentioned above in the polymerization reaction.

The amount of the liquid medium is preferably 0.1 to 30% by mass, more preferably 0.2 to 20% by mass, and even more preferably 0.3 to 15% by weight, based on the total amount of the compound (A), compound (B), and compound (Bm).

In the present specification, "(the state of) being dissolved or dispersed" means a state in which a homogenous state is visually observed 10 minutes or more after stirring (that is, a state in which a non-homogenous state is not macroscopically observed).

EXAMPLES

The present invention is described in more detail with reference to Examples. However, the scope of the invention is not limited to these Examples.

The meanings of symbols and abbreviations in the examples are shown below.

The present invention is described in more detail with reference to Examples and Comparative Examples; however, the present invention is not limited thereto.

The meanings of the symbols and abbreviations in the Examples are as follows.

StA: $C_{18}H_{37}OCOCH{=}CH_2$ (stearyl acrylate)

MEK: methyl ethyl ketone

AIBM: azobisisobutyronitrile

TMPTA: trimethylolpropane triacrylate

BuMA: butyl methacrylate

Example 1

Production of Thin Film Comprising Copolymer of StA and Fine Particle, and TMPTA, at a Copolymer/TMPTA Ratio of 90/10 (w/w)

Preparation of Solution of Copolymer of StA and Fine Particle 10.12 g of StA, 5.04 g of silica fine particles having a radical polymerizable group on the surface and having a number average primary particle size of 12 nm (apparent density: 0.033 g/cm$^3$), and 184.89 g of MEK were placed in a reactor with a stirrer. The reactor was purged with nitrogen, and heated to 78° C. Further, 0.50 g of AIBN was added thereto, and a reaction was allowed to proceed for 6 hours.

Preparation of Photosensitive Solution 0.042 g of TMPTA, 0.022 g of 2-methyl-1-(4-methylthiophenyl)-2-morpholinopropan-1-one as an alkylphenone-based photopolymerization initiator, and 12.25 g of MEK were placed in a vial; and mixed. Further, 3.90 g of the copolymer solution was added and mixed to prepare a photosensitive solution.

Production of Coating Film

The photosensitive solution was applied to an aluminum substrate (a plate having a smooth surface according to the visual observation) by the spraying method. The coated substrate was then irradiated with ultraviolet rays at 1,800 mJ/$cm^2$ using a UV irradiation device.

Example 2

Production of Thin Film Comprising Copolymer of StA and Fine Particle, and TMPTA, at a Copolymer/TMPTA Ratio of 80/20 (w/w)

A coating film was prepared in the same manner as in Example 1, except that the amounts of the following components described in the section "Preparation of Photosensitive Solution" were changed as follows: 0.079 g of TMPTA, 0.022 g of the alkylphenone-based photopolymerization initiator, 12.53 g of MEK, and 3.31 g of the copolymer solution.

Example 3

Production of Thin Film Comprising Copolymer of StA And Fine Particle, and TMPTA, at a Copolymer/TMPTA Ratio of 90/10 (w/w)

A coating film was prepared in the same manner as in Example 1, except that the bar coating method was used in place of the spraying method described above in the section "Production of Coating Film."

Example 4

Production of Thin Film Comprising Copolymer of StA and Fine Particle, and TMPTA, at a Copolymer/TMPTA Ratio of 80/20 (w/w)

A coating film was prepared in the same manner as in Example 2, except that the bar coating method was used in place of the spraying method described above in the section "Production of Coating Film."

Example 5

Production of Thin Film Comprising Copolymer of BuMA and Fine Particle, and TMPTA, at a Copolymer/TMPTA Ratio of 90/10 (w/w)

Preparation of Solution of Copolymer of BuMA and Fine Particle 4.35 g of BuMA, 1.98 g of silica fine particles having a radical polymerizable group on the surface and having a number average primary particle size of 12 nm (apparent density: 0.033 g/$cm^3$), and 75.74 g of MEK were placed in a reactor with a stirrer. The reactor was purged with nitrogen, and heated to 78° C. Further, 0.21 g of AIBN was added thereto, and a reaction was allowed to proceed for 6 hours.

Preparation of Photosensitive Solution 0.041 g of TMPTA, 0.018 g of an alkylphenone-based photopolymerization initiator, and 5.18 g of MEK were placed in a vial; and mixed. Further, 10.76 g of the copolymer solution was added and mixed to prepare a photosensitive solution.

Production of Coating Film

A coating film was produced in the same procedure as in Example 1.

Example 6

Production of Thin Film Comprising Copolymer of BuMA and Fine Particle, and TMPTA, at a Copolymer/TMPTA Ratio of 80/20 (w/w)

A coating film was prepared in the same manner as in Example 5, except that the amounts of the following components described in the section "Preparation of Photosensitive Solution" were changed as follows: 0.080 g of TMPTA, 0.019 g of the alkylphenone-based photopolymerization initiator, 6.38 g of MEK, and 9.69 g of the copolymer solution.

Comparative Example 1

Production of Thin Film Comprising Copolymer of Rf(C6)MA and Fine Particle

Preparation of Solution of Copolymer of Rf(C6)MA and Fine Particle 25.46 g of $C_6F_{13}CH_2CH_2OCOC(CH_3){=}CH_2$ (hereinafter sometimes simply referred to as Rf(C6)methacrylate), 12.70 g of silica fine particles having a radical polymerizable group on the surface and having a number average primary particle size of 12 nm (apparent density: 0.033 g/$cm^3$), and 663.49 g of perfluorobutylethyl ether were placed in a reactor with a stirrer. The reactor was purged with nitrogen, and heated to 70° C. Further, 1.27 g of AIBN was added thereto, and a reaction was allowed to react for 6 hours.

7.47 g of the polymerization solution and 9.92 g of perfluorobutylethyl ether were placed in a vial and mixed to disperse a copolymer of Rf(C6)methacrylate and fine particles. An aluminum substrate was then immersed in the solution to form a coating film.

Comparative Example 2

Production of Thin Film of Rf(C6)-MA Polymer

Preparation of (Rf(C6)MA Polymer)

25.00 g of Rf(C6)MA and 75.00 g of perfluorobutylethyl ether were placed in a reactor with a stirrer. The reactor was purged with nitrogen, and heated to 70° C. Further, 0.136 g of AIBN was added thereto, and a reaction was allowed to proceed for 6 hours.

Production of Coating Film 0.50 g of the polymerization solution and 11.5 g of perfluorobutylethyl ether were placed in a vial. An aluminum substrate (having a smooth surface) was immersed in the solution, and air-dried at room temperature for 30 minutes to form a coating film.

Comparative Example 3

Production of Thin Film Comprising a Copolymer of StA and Fine Particle, and TMPTA, at a Copolymer/TMPTA Ratio of 50/50 (w/w)

A coating film was prepared in the sane manner as in Example 3, except that the amounts of the following components described above in the section "Preparation of Photosensitive Solution" were changed as follows: 0.20 g of TMPTA, 0.019 g of the alkylphenone-based photopolymerization initiator, 13.89 g of MEK, and 2.15 g of the copolymer solution.

Comparative Example 4

Production of Thin Film Comprising a Copolymer of BuMA and Fine Particle, and TMPTA, at a Copolymer/TMPTA Ratio of 50/50 (w/w)

A photosensitive solution was prepared in the same manner as in Example 4, except that the amounts of the following components described above in the section "Preparation of Photosensitive Solution" were changed as follows: 0.21 g of TMPTA, 0.022 g of the alkylphenone-based photopolymerization initiator, 9.92 g of MEK, and 6.13 g of the copolymer solution.

Comparative Example 5

Production of Thin Film Comprising StA Polymer

Preparation of StA Polymer

A coating film was prepared in the same manner as in Comparative Example 2, except that 25.00 g of StA was used in place of Rf(C6)MA, 75.00 g of MEK was used in place of perfluorobutylethyl ether, and the amount of AIBN was changed to 0.18 g.

Preparation of Coating Film

A thin film was produced in the same manner as in Comparative Example 2, except that MEK was used in place of perfluorobutyl ethyl ether.

Comparative Example 6

Production of Thin Film of BuMA Polymer

Preparation of BuMA Polymer

A coating film was prepared in the same manner as in Comparative Example 2, except that 25.00 g of BuMA was used in place of Rf(C6)MA, 75.00 g of MEK was used in place of perfluorobutylethyl ether, and the amount of AIBN was changed to 0.40 g.

Preparation of Coating Film

A thin film was prepared in the same manner as in Comparative Example 2, except that MEK was used in place of perfluorobutyl ethyl ether.

Test Examples 1 to 43

Various physical properties described below of test pieces obtained in Examples 1 to 6 and Comparative Examples 1 to 6 were determined by the methods described in the individual sections.

Measurement of Water Contact Angle (Test Examples 1 to 12)

The water contact, angle of test pieces of the examples shown in Table 1 was measured.

The method for measuring the contact angle used was the method described in detail in the above section "Embodiment of the Invention."

The following table shows the results.

TABLE 1

| | Coating film | Water (2 μl) |
|---|---|---|
| Test Example 1 | Example 1 | 150.1 ± 3.1 |
| Test Example 2 | Example 2 | 140.3 ± 3.0 |
| Test Example 3 | Example 3 | 157.7 ± 0.8 |
| Test Example 4 | Example 4 | 132.6 ± 3.4 |
| Test Example 5 | Example 5 | 115.9 ± 2.8 |
| Test Example 6 | Example 6 | 128.3 ± 2.3 |
| Test Example 7 | Comparative Example 1 | 162.3 ± 2.0 |
| Test Example 8 | Comparative Example 2 | 112.6 ± 0.3 |
| Test Example 9 | Comparative Example 3 | 96.4 ± 1.5 |
| Test Example 10 | Comparative Example 4 | 90.4 ± 2.8 |
| Test Example 11 | Comparative Example 5 | 89.3 ± 0.4 |
| Test Example 12 | Comparative Example 6 | 72.5 ± 0.8 |

Calculation of Wenzel Roughness Factor (Test Examples 13 to 24)

Using a VK-9710 (product name, produced by Keyence Corporation) color 3D laser microscope, the ratio of the surface area of the prepared test sample to the surface area of the substrate of the test piece of each example (Wenzel roughness factor) shown in the following table was calculated in a 351.4 μm×351.5 μm quadrangular area.

Table 2 shows the results.

TABLE 2

| | Coating film | Wenzel roughness factor |
|---|---|---|
| Test Example 13 | Example 1 | 2.84 |
| Test Example 14 | Example 2 | 4.38 |
| Test Example 15 | Example 3 | 2.30 |
| Test Example 16 | Example 4 | 1.77 |
| Test Example 17 | Example 5 | 1.48 |
| Test Example 18 | Example 6 | 2.02 |
| Test Example 19 | Comparative Example 1 | 3.08 |
| Test Example 20 | Comparative Example 2 | 1.06 |
| Test Example 21 | Comparative Example 3 | 1.46 |
| Test Example 22 | Comparative Example 4 | 1.24 |
| Test Example 23 | Comparative Example 5 | 1.11 |
| Test Example 24 | Comparative Example 6 | 1.08 |

Calculation of Ra (Test Examples 25 to 36)

Using the apparatuses described below, the test piece of each example shown in Table 3 was measured in an area of 526.929 μm×702.801 μm, and Ra was calculated. The table below show the results.

Devices: VK-9710 (trade name; produced by Keyence) color 3D laser microscope, and microscope unit attached to MUL00201 (trade name; produced by Nikon).

TABLE 3

| | Coating film | Ra (μm) |
|---|---|---|
| Test Example 25 | Example 1 | 6.14 |
| Test Example 26 | Example 2 | 8.04 |
| Test Example 27 | Example 3 | 3.25 |
| Test Example 28 | Example 4 | 2.48 |
| Test Example 29 | Example 5 | 3.87 |
| Test Example 30 | Example 6 | 4.78 |
| Test Example 31 | Comparative Example 1 | 7.34 |
| Test Example 32 | Comparative Example 2 | 1.55 |
| Test Example 33 | Comparative Example 3 | 2.11 |
| Test Example 34 | Comparative Example 4 | 1.73 |
| Test Example 35 | Comparative Example 5 | 1.34 |
| Test Example 36 | Comparative Example 6 | 1.27 |

Rubbing Test (Test Examples 37 to 43)

A PET film (trade name: U-46, produced by Toray Industries, Inc.) was mounted on the holder of a rubbing tester ("Abrasion resistance tester 151E, triple series"; produced by Imoto Machinery Co., Ltd.; area in contact with a test sample: 1 $cm^2$). The surface of test pieces of the examples shown in the following table was wiped by rubbing with the PET film a predetermined number of times under a load of 100 g. The angle of water with respect to each test piece was then measured to evaluate the abrasion resistance to wiping. The abrasion resistance performance was defined as the number of times of abrasion (the number of durable times) in which the average static contact angle in five measurements was 100° or more.

Table 4 shows the measurement results.

TABLE 4

| | Coating film | Number of durable times |
|---|---|---|
| Test Example 37 | Example 1 | ≥20000 |
| Test Example 38 | Example 2 | ≥20000 |
| Test Example 39 | Example 3 | ≥20000 |
| Test Example 40 | Example 4 | ≥20000 |
| Test Example 41 | Example 5 | ≥20000 |
| Test Example 42 | Example 6 | ≥20000 |
| Test Example 43 | Comparative Example 1 | 1250 |

Measurement of Fluorine Content (XPS Analysis) (Test Examples 44 to 55)

The fluorine content was measured by subjecting the test pieces of Examples 1 to 6 and Comparative Examples 1 to 6 to XPS analysis using the following device.

Measuring device: ESCA3400 (product name; produced by Shimadzu Corporation)

Conditions

Ejection Angle: 90°

Table 5 shows the results.

The test pieces of Examples 1 to 6 and Comparative Examples 3 to 6 all had a fluorine content of 1 mass % or less.

In contrast, the test pieces of Comparative Examples 1 and 2 had a fluorine content of more than 1 mass %.

TABLE 5

| | Coating film | Fluorine content |
|---|---|---|
| Test Example 44 | Example 1 | ≤1 wt % |
| Test Example 45 | Example 2 | ≤1 wt % |
| Test Example 46 | Example 3 | ≤1 wt % |
| Test Example 47 | Example 4 | ≤1 wt % |
| Test Example 48 | Example 5 | ≤1 wt % |
| Test Example 49 | Example 6 | ≤1 wt % |
| Test Example 50 | Comparative Example 1 | >1 wt % |
| Test Example 51 | Comparative Example 2 | >1 wt % |
| Test Example 52 | Comparative Example 3 | ≤1 wt % |
| Test Example 53 | Comparative Example 4 | ≤1 wt % |
| Test Example 54 | Comparative Example 5 | ≤1 wt % |
| Test Example 55 | Comparative Example 6 | ≤1 wt % |

The invention claimed is:

1. A composition comprising a polymer containing structural units derived from (A) at least one modified particle comprising a core particle and one or more polymerizable groups (a) on the surface of the particle, and not containing fluorine, the core particle being a silica fine particle; and (Bs) at least one compound containing one polymerizable group (b) in the molecule, and not containing fluorine;

the composition further comprising (Bm) a compound containing two or more polymerizable groups in the molecule, the core particle having a number average particle size in the range of 5 to 1000 nm, the compound (Bm) being present in an amount of 10 to 30 parts by mass per 100 parts by mass of the polymer, the compound (Bs) comprising at least one member selected from the group consisting of:

$CH_3O—CO—C(—CH_3)═CH_2$, $C_2H_5O—CO—C(—CH_3)═CH_2$, $C_3H_7O—CO—C(—CH_3)═CH_2$, $C_4H_9O—CO—C(—CH_3)═CH_2$, $C_{18}H_{37}O—CO—CH═CH_2$, and $C_{18}H_{37}O—CO—C(—CH_3)═CH_2$, the compound (Bm) comprising at least one member selected from the group consisting of:

$CH_3—CH_2—C—(CH_2OCO—CH═CH_2)_3$, $C(—CH_2OCO—CH═CH_2)_4$, and $O[—CH_2(—CH_2OCO—CH═CH_2)_3]_2$.

2. The composition according to claim 1, wherein the composition forms a coating film when combined with (Bm) and cured, wherein the coating film has a fluorine content of less than 1 wt %, a water contact angle of 115° or more, wherein the water contact angle is measured with a 2 μL droplet of water, and an abrasion resistance whereby the water contact angle is 100° or more after the coating film is rubbed with a PET film under a load of 100 gf/$cm^2$ and for 1500 reciprocations, and wherein the coating film satisfies at least one of the following regarding surface roughness indices:

(a) an average surface roughness Ra of 1.6 m or more; and (b) a Wenzel roughness factor of 1.2 or more.

3. A kit comprising (A) at least one modified particle comprising a core particle and one or more polymerizable groups (a) on the surface of the particle, and not containing fluorine, the core particle being a silica fine particle;

the core particle having a number average particle size in the range of 5 to 1000 nm; and (Bs) at least one compound containing one or more polymerizable groups (b) in the molecule, and not containing fluorine; and (Bm) at least one compound containing two or more polymerizable groups (b) in the molecule, and not containing fluorine, the compound (Bm) being disposed apart from the modified particle (A) and compound (Bs), the compound (Bm) being present in an amount of 10 to 30 parts by mass per 100 parts by total mass of the (A) and (Bs), the compound (Bs) comprising at least one member selected from the group consisting of:

$CH_3O—CO—C(—CH_3)═CH_2$, $C_2H_5O—CO—C(—CH_3)═CH_2$, $C_3H_7O—CO—C(—CH_3)═CH_2$, $C_4H_9O—CO—C(—CH_3)═CH_2$, $C_{18}H_{37}O—CO—CH═CH_2$, and $C_{18}H_{37}O—CO—C(—CH_3)═CH_2$, the compound (Bm) comprising at least one member selected from the group consisting of:

$CH_3—CH_2—C—(CH_2OCO—CH═CH_2)_3$, $C(—CH_2OCO—CH═CH_2)_4$, and $O[—CH_2(—CH_2OCO—CH═CH_2)_3]_2$.

4. A method for subjecting an article to a liquid repellent treatment, comprising applying, to a part of the surface or to the entire surface of the article, (A) at least one modified particle comprising a core particle and one or more polymerizable groups (a) on the surface of the particle, and not containing fluorine, the core particle being a silica fine particle;

the core particle having a number average particle size in the range of 5 to 1000 nm; and (B) at least one compound containing one or more polymerizable groups (b) in the molecule, and not containing fluorine;

or a reaction product of particle (A) and compound (B); and (Bm) at least one compound containing two or more polymerizable groups (b) in the molecule, and not containing fluorine, the compound (Bm) being present in an amount of 10 to 30 parts by mass per 100 parts by total mass of the (A) and (B), the compound (B) comprising at least one member selected from the group consisting of:

$CH_3O—CO—C(—CH_3)═CH_2$,
$C_2H_5O—CO—C(—CH_3)═CH_2$,
$C_3H_7O—CO—C(—CH_3)═CH_2$,
$C_4H_9O—CO—C(—CH_3)═CH_2$,
$C_{18}H_{37}O—CO—CH═CH_2$, and
$C_{18}H_{37}O—CO—C(—CH_3)═CH_2$, the compound (Bm) comprising at least one member selected from the group consisting of:

$CH_3—CH_2—C—(CH_2OCO—CH═CH_2)_3$,
$C(—CH_2OCO—CH═CH_2)_4$, and
$O[—CH_2(—CH_2OCO—CH═CH_2)_3]_2$.

5. A coating composition comprising at least one member selected from the group consisting of:

(A) at least one modified particle comprising a core particle and one or more polymerizable groups (a) on the surface of the particle, and not containing fluorine, the core particle being a silica fine particle;

the core particle having a number average particle size in the range of 5 to 1000 nm; and (B) at least one compound containing one or molecule, and not containing fluorine;

or a reaction product of particle (A) and compound (B); and (Bm) at least one compound containing two or more polymerizable groups (b) in the molecule, and not containing fluorine, the compound (Bm) being present in an amount of 10 to 30 parts by mass per 100 parts by total mass of the (A) and (B), the compound (B) comprising at least one member selected from the group consisting of:

$CH_3O—CO—C(—CH_3)═CH_2$,
$C_2H_5O—CO—C(—CH_3)═CH_2$,
$C_3H_7O—CO—C(—CH_3)═CH_2$,
$C_4H_9O—CO—C(—CH_3)═CH_2$,
$C_{18}H_{37}O—CO—CH═CH_2$, and
$C_{18}H_{37}O—CO—C(—CH_3)═CH_2$, the compound (Bm) comprising at least one member selected from the group consisting of:

$CH_3—CH_2—C—(CH_2OCO—CH═CH_2)_3$,
$C(—CH_2OCO—CH═CH_2)_4$, and
$O[—CH_2(—CH_2OCO—CH═CH_2)_3]_2$.

6. A composition for liquid-repellent treatment comprising at least one member selected from the group consisting of:

(A) at least one modified particle comprising a core particle and one or more polymerizable groups (a) on the surface of the particle, and not containing fluorine, the core particle being a silica fine particle;

the core particle having a number average particle size in the range of 5 to 1000 nm; and (B) at least one compound containing one or more polymerizable groups (b) in the molecule, and not containing fluorine;

or a reaction product of particle (A) and compound (B); and (Bm) at least one compound containing two or more polymerizable groups (b) in the molecule, and not containing fluorine, the compound (Bm) being present in an amount of 10 to 30 parts by mass per 100 parts by total mass of the (A) and (B), the compound (B) comprising at least one member selected from the group consisting of:

$CH_3O—CO—C(—CH_3)═CH_2$,
$C_2H_5O—CO—C(—CH_3)═CH_2$,
$C_3H_7O—CO—C(—CH_3)═CH_2$,
$C_4H_9O—CO—C(—CH_3)═CH_2$,
$C_{18}H_{37}O—CO—CH═CH_2$, and
$C_{18}H_{37}O—CO—C(—CH_3)═CH_2$, the compound (Bm) comprising at least one member selected from the group consisting of:

$CH_3—CH_2—C—(CH_2OCO—CH═CH_2)_3$,
$C(—CH_2OCO—CH═CH_2)_4$, and
$O[—CH_2(—CH_2OCO—CH═CH_2)_3]_2$.

7. A coating film of the composition according to claim 1, having a fluorine content of less than 1 wt %, a water contact angle of 115' or more, wherein the water contact angle is measured with a 2 μL droplet of water, and an abrasion resistance whereby the water contact angle of is 1000 or more after the coating film is rubbed with a PET film under a load of 100 gf/cm$^2$ and for 1500 reciprocation, and wherein the coating film satisfies at least one of the following regarding surface roughness indices:

(a) an average surface roughness Ra of 1.6 m or more; and (b) a Wenzel roughness factor of 1.2 or more.

8. The coating film according to claim 7, wherein the average surface roughness Ra is in the range of 1.6 to 20 μm.

9. The coating film according to claim 7, wherein the Wenzel roughness factor is in the range of 1.6 to 10.

10. The coating film according to claim 7, wherein the coating film has an abrasion resistance whereby the water contact angle is 120° or more after the coating film is rubbed with a PET film under a load of 100 gf/cm$^2$ and for 1500 reciprocations.

11. The coating film according to claim 7, wherein the coating film has an abrasion resistance whereby the water contact angle is 1500 or more after the coating film is rubbed with a PET film under a load of 100 gf/cm$^2$ and for 1500 reciprocations.

12. The coating film according to claim 7, wherein in the surface friction with a PET film under a load of 100 gf/cm$^2$, the number of times of surface friction that allows the coating film to maintain a water contact angle of 1000 or more is 20000 reciprocations or more.

13. The composition according to claim 1, wherein R represents a linear or branched $C_{16}$-$C_{22}$ alkyl group optionally having one or more oxygen atoms.

14. The composition according to claim 3,
wherein R represents a linear or branched $C_{16}$-$C_{22}$ alkyl group optionally having one or more oxygen atoms.

15. The composition according to claim 4,
wherein R represents a linear or branched $C_{16}$-$C_{22}$ alkyl group optionally having one or more oxygen atoms.

16. The composition according to claim 5,
wherein R represents a linear or branched $C_{16}$-$C_{22}$ alkyl group optionally having one or more oxygen atoms.

17. The composition according to claim 6,
wherein R represents a linear or branched $C_{16}$-$C_{22}$ alkyl group optionally having one or more oxygen atoms.

* * * * *